(12) United States Patent
Hultgren

(10) Patent No.: US 10,086,143 B2
(45) Date of Patent: Oct. 2, 2018

(54) PERIMETER FILL SYRINGE

(71) Applicant: PURDUE RESEARCH FOUNDATION, West Lafayette, IN (US)

(72) Inventor: Kyle Emerson Hultgren, Fishers, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/054,221

(22) Filed: Feb. 26, 2016

(65) Prior Publication Data
US 2016/0250416 A1    Sep. 1, 2016

Related U.S. Application Data

(60) Provisional application No. 62/126,028, filed on Feb. 27, 2015.

(51) Int. Cl.
*A61M 5/31* (2006.01)

(52) U.S. Cl.
CPC ... *A61M 5/3129* (2013.01); *A61M 2005/3126* (2013.01); *A61M 2205/19* (2013.01); *A61M 2205/584* (2013.01); *A61M 2205/586* (2013.01)

(58) Field of Classification Search
CPC .. A61M 5/3129; A61M 5/19; A61M 25/0026; A61M 5/31511; A61M 2205/19
See application file for complete search history.

(56) References Cited

U.S. PATENT DOCUMENTS

| | | | | |
|---|---|---|---|---|
| 3,738,535 | A | * | 6/1973 | Nicholls ........... A61M 5/31596 222/137 |
| 3,749,084 | A | * | 7/1973 | Cucchiara .......... A61B 5/02755 600/575 |
| 4,178,071 | A | * | 12/1979 | Asbell ................ A61M 5/3129 359/442 |

\* cited by examiner

*Primary Examiner* — Laura Bouchelle
*Assistant Examiner* — Tasnim M Ahmed
(74) *Attorney, Agent, or Firm* — Purdue Research Foundation

(57) ABSTRACT

A perimeter fill syringe is disclosed, wherein the syringe includes a solid core, allowing fluid to fill an area around the perimeter of the syringe barrel, enabling a wider diameter for the barrel thus increasing the visibility of the markings and ease of handling by a user.

20 Claims, 13 Drawing Sheets

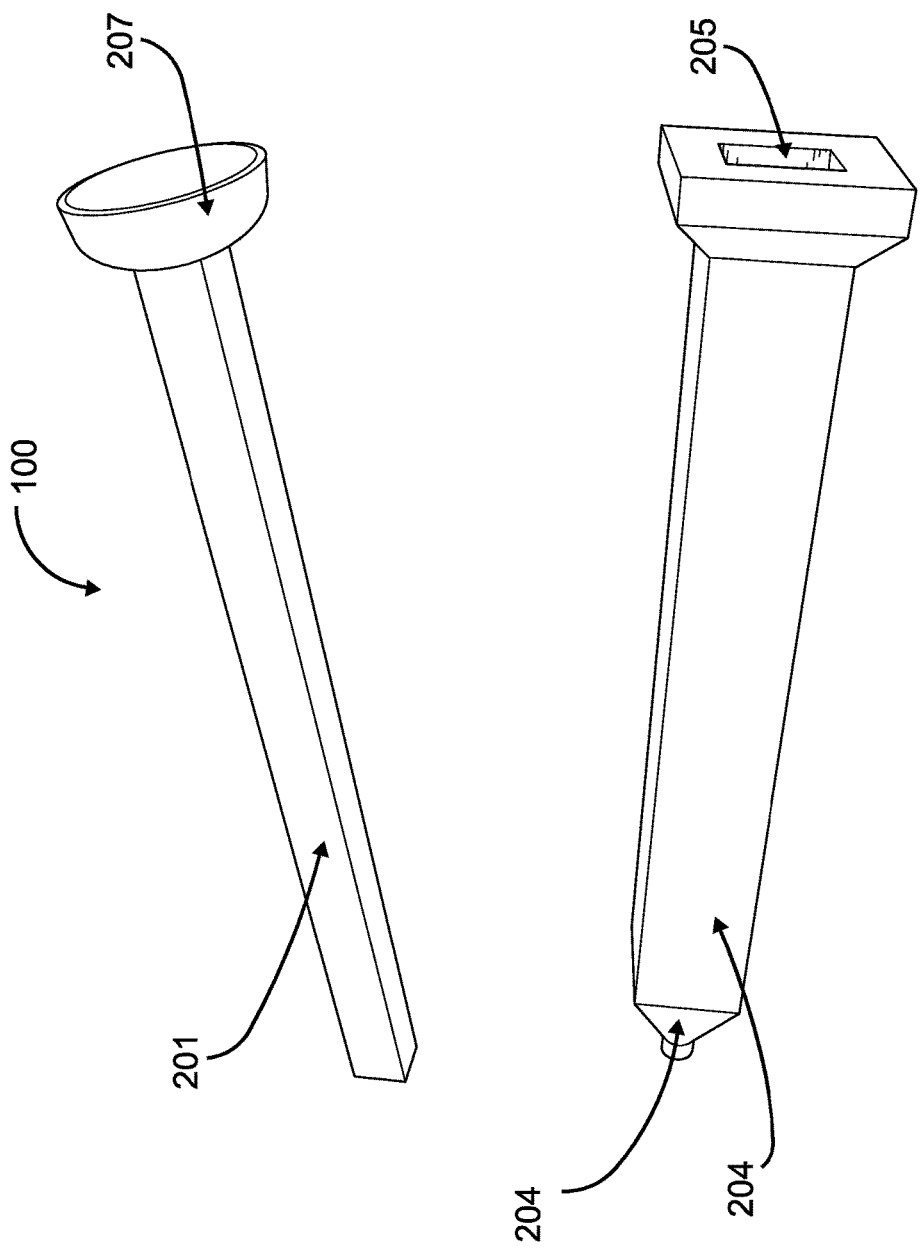

PERIMETER FILL SYRINGE

CROSS-REFERENCE TO RELATED APPLICATIONS

The present patent application is related to and claims the priority benefit of U.S. Provisional Patent Application Ser. No. 62/126,028, filed Feb. 27, 2015, the contents of which is hereby incorporated by reference in its entirety into this disclosure.

TECHNICAL FIELD

The present disclosure generally relates to syringes, and in particular to a syringe with a solid core, allowing fluid to fill an area around the perimeter of the syringe barrel, enabling a wider diameter for the barrel thus increasing the visibility of the markings and ease of handling by the patient.

BACKGROUND

This section introduces aspects that may help facilitate a better understanding of the disclosure. Accordingly, these statements are to be read in this light and are not to be understood as admissions about what is or is not prior art.

Health care providers administering medications to patients must exercise great care in determining the amount medication to inject into the patient's body. Similarly, for example, diabetic patients must likewise take great care to ensure the amount of insulin injected into their bodies is of the appropriate dosage. Unfortunately, however, many patients suffer ailments (e.g., failing eyesight) that make it difficult, and often dangerous, to adequately administer the required dosage of medication into their bodies. Such consequences can be extended to all drugs that must be administered via a syringe. Given that an improper dosage can result in serious consequences, it is critical that both health care providers and patients themselves be able to clearly and accurately determine the amount of medications loaded in a syringe prior to injection.

Additionally, health care providers and patients themselves who must administer a drug via a syringe continually face the risk of accidental needle sticks. Even when cautious, there is always a chance that the person administering the drug via a needle syringe will slip and accidentally stick himself or another person. Every year in the United States, 44,000 to 98,000 people die as a result of medical error. Medication errors are a leading form of medical harm with over 1.5 million adverse drug events associated with medication use occurring every year. The medication use process is complex and difficult to navigate, even for trained professionals. Some medications are more prone to error than others for patients and professionals alike, and these medications earn the title high risk medications. Every year without fail, more errors associated with injectable insulin are reported than any other medication. This is exceptionally troubling given the nature of the medication insulin. It is an endogenous hormone in the human body that we supplement for patients with diabetes who do not synthesize sufficient quantities or for those who have developed an insensitivity to insulin in their body. Small volumes of insulin, measured and dosed to patients in terms of units of insulin, can have profound effects on our bodies. Volumes as small as 10 units or less can be enough to send someone into a state of hypoglycemia, a condition that if uncorrected can have dramatic effects and in some instances, if not reversed, be fatal. This range between where the medication is useful to patients and the point at which it becomes toxic is known as a therapeutic window. Insulin has one of the narrowest therapeutic windows but one of the widest ranges of dosing as patients can require as little as 2 units and some could require over 100 units.

Combined with the narrow therapeutic window of insulin, we additionally complicate this process by manufacturing more than one concentration of insulin. Currently, 100 unit/mL and 500 unit/mL concentrations are readily available with a 200 unit/mL concentration available in the EU that may someday soon be available in the United States. Administering these doses requires drawing insulin up into an insulin syringe, which is a device specifically designed and marked for volumes of 100 unit/mL insulin. Therefore, a patient needing to administer 16 units could draw up precisely this amount into their syringe from a multi-dose vial and administer it to themselves. Patients that receive more than 200 units of insulin per day may elect to be placed on U500 (500 unit/mL insulin) to minimize the volume of fluid injected daily. In order to perform this process, these patients still must use a U100 (100 unit/mL) insulin syringe to accomplish this task.

Thus, there remains an unmet need for syringes that enable safe, reliable administration of a drug to protect against both improper dosage and inadvertent needle sticks.

SUMMARY

In one aspect, a perimeter fill syringe is presented. The perimeter fill syringe includes a top end, wherein the top end is configured to be coupled to a syringe needle, and a bottom end, wherein the bottom end is configured to be coupled to a plunger. The plunger is configured to be slidably coupled to the perimeter fill syringe. The perimeter fill syringe also includes an outer shell that is along the length between the top and the bottom end of the perimeter fill syringe. The perimeter fill syringe also includes a core that is encased within the outer shell.

In another aspect, a method for reliably administering medication and dosage to a patient is presented. The method includes utilizing the presented perimeter fill syringe of a particular design to administer the medication.

BRIEF DESCRIPTION OF THE FIGURES

FIG. 8 shows an alternate embodiment of the perimeter fill syringe shown in FIG. 7, but in FIG. 8, the shape of the perimeter fill syringe is rectangular.

DETAILED DESCRIPTION

Figure 1:
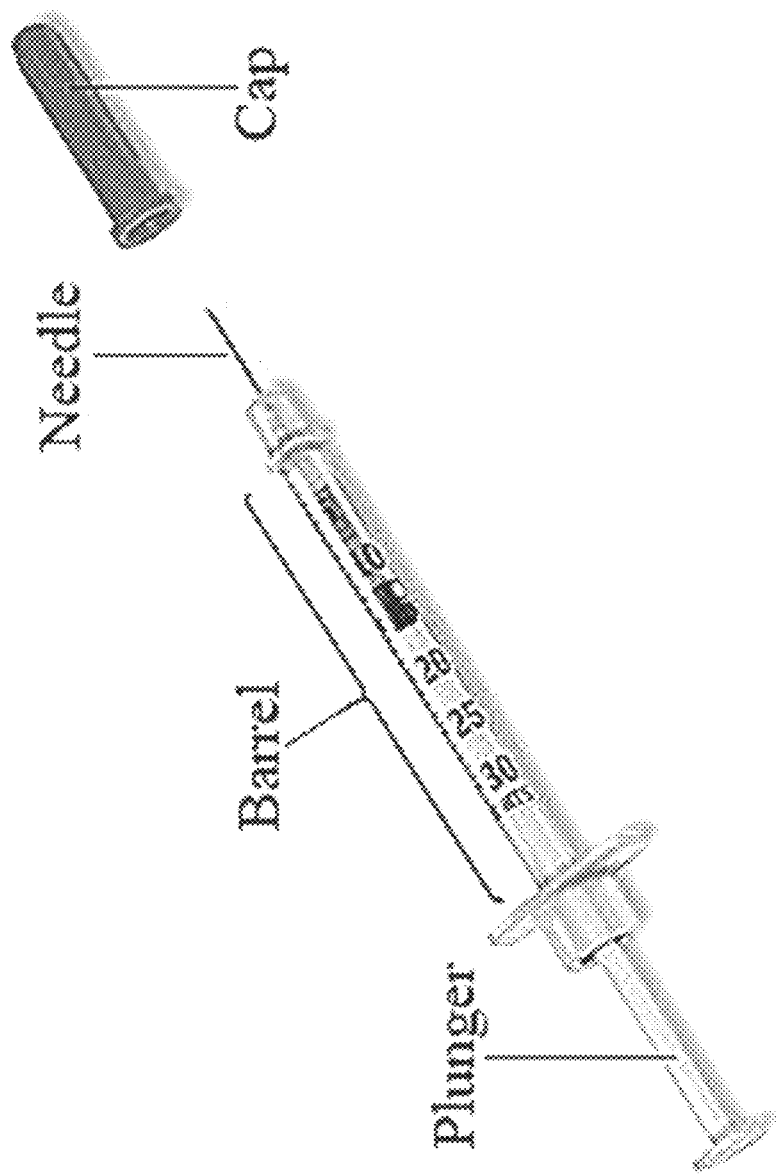
FIG. 1 is an image of an insulin syringe in common use.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In response to the unmet need for a syringe design that enable safe, reliable administration of a drug to protect against both improper dosage and inadvertent needle sticks, such a novel syringe design is disclosed herein. For demonstration purposes, the herein described novel syringe design is an insulin syringe. However, it should be appreciated that the applications for the herein described novel syringe extends beyond insulin syringes and can apply to medications of all types that are to be administered via a syringe.

Referring to FIG. 1, which is an image of an insulin syringe in common use, current syringes comprise a hollow barrel and a solid plunger used to push fluid out of a nozzle at the tip. There are numerous shortcomings in the current insulin syringe designs. First, the size of the syringe is quite small. It has a narrow diameter cylinder with markings that wrap almost completely around the barrel of the syringe. This small size can be difficult to handle for both health care providers and patients of all ages. Notably, complications of diabetes, specifically in those patients who may already have high insulin demand (in excess of 200 units per day), include blurred vision and neuropathy, or pain and loss of sensation in their fingers and toes. These patient conditions make the current syringe design far less than optimal for the safe, ergonomic handling of a device that is intended to inject a drug with a narrow therapeutic window.

Second, these syringes can be used for both U100 and U500 concentrations. For example, if a health care provider drew up 100 units of U500 in one syringe and 20 units of U100 into separate syringes (same volumes of clear liquid) and walked away to attend to another task (e.g., answer a ringing phone), the syringes would be indistinguishable upon the health care provider's return. If the health care provider did not remember which was which, one represents a lethal dose for one patient while the other represents a dose far too low to combat the conditions of the other patient. Without any visual cues or "forcing functions" to indicate differently concentrated insulin doses is a formula for catastrophe. A forcing function would be any discernable difference between syringes such as shape, size, color, structure, or any other means of immediately noticing a difference beyond having to remember.

Third, the current U100 syringes require computations to be made in order to achieve the correct dose. In order for a health care provider or a patient to achieve a 100 unit dose of U500 insulin, they would need 0.2 mL of insulin at this concentration to achieve this. However, 0.2 mL in a U100 syringe is labeled on the barrel as only being 20 units. Such requirements are accompanied by risk that errors can be made in the computations and can thus lead to disastrous results, should an error be made.

Figure 2A:
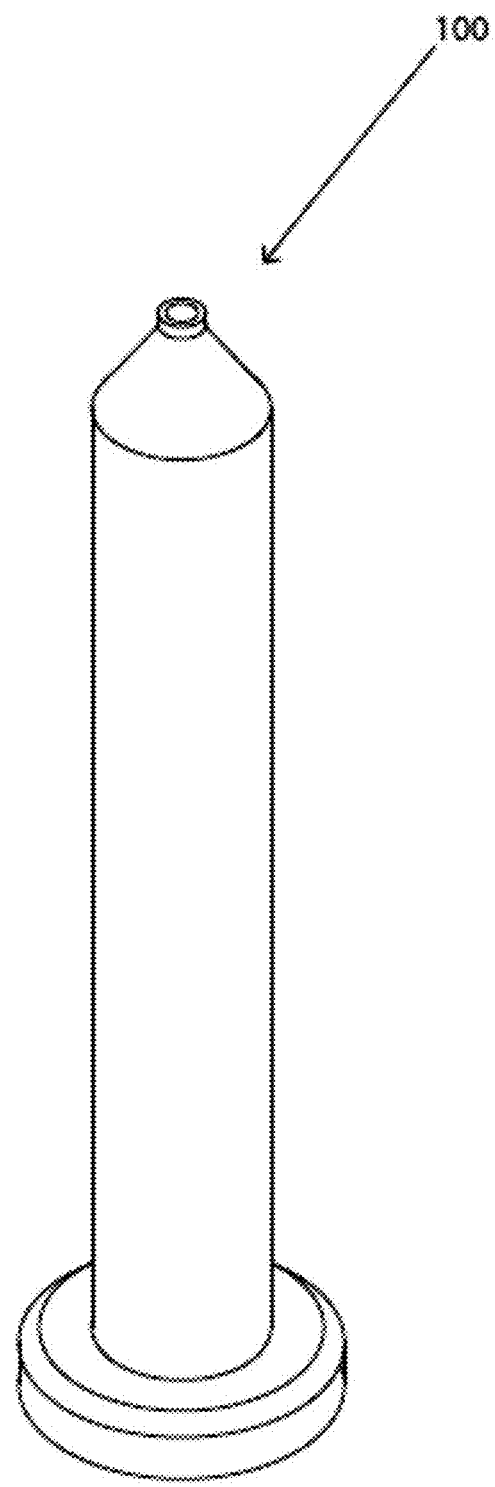
FIG. 2A is an image of one embodiment of the perimeter fill syringe that is cylindrical in shape.
Figure 2B:
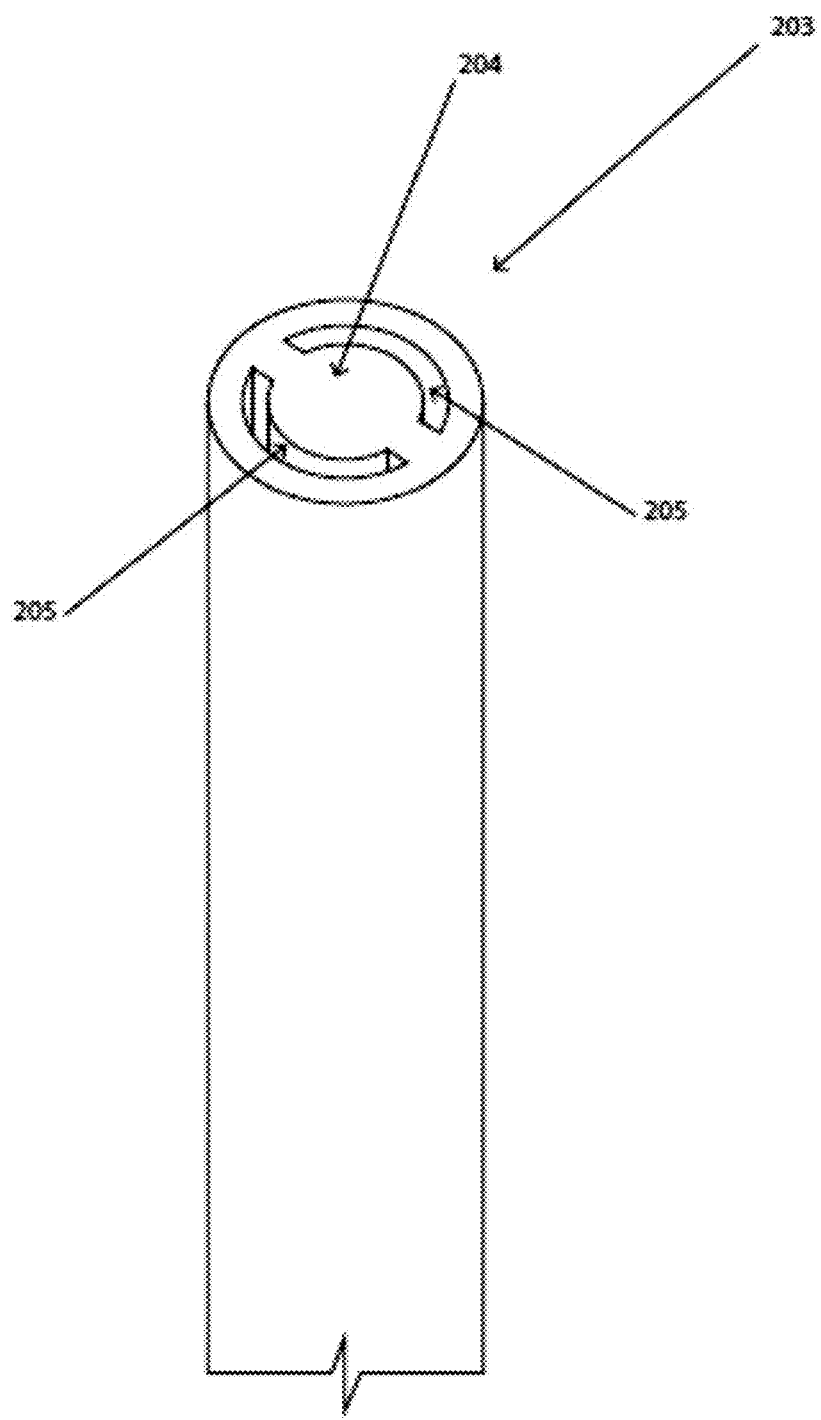
FIG. 2B is an image of an embodiment of the top end of the outer shell of the perimeter fill syringe.
Figure 3A:
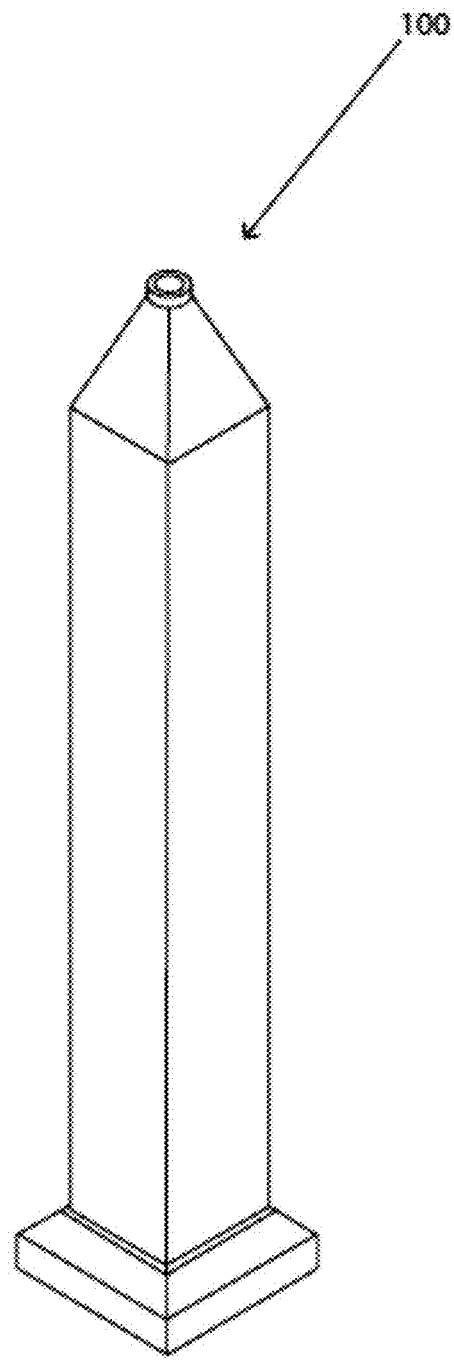
FIG. 3A is an image of one embodiment of the perimeter fill syringe that is rectangular in shape.
Figure 3B:
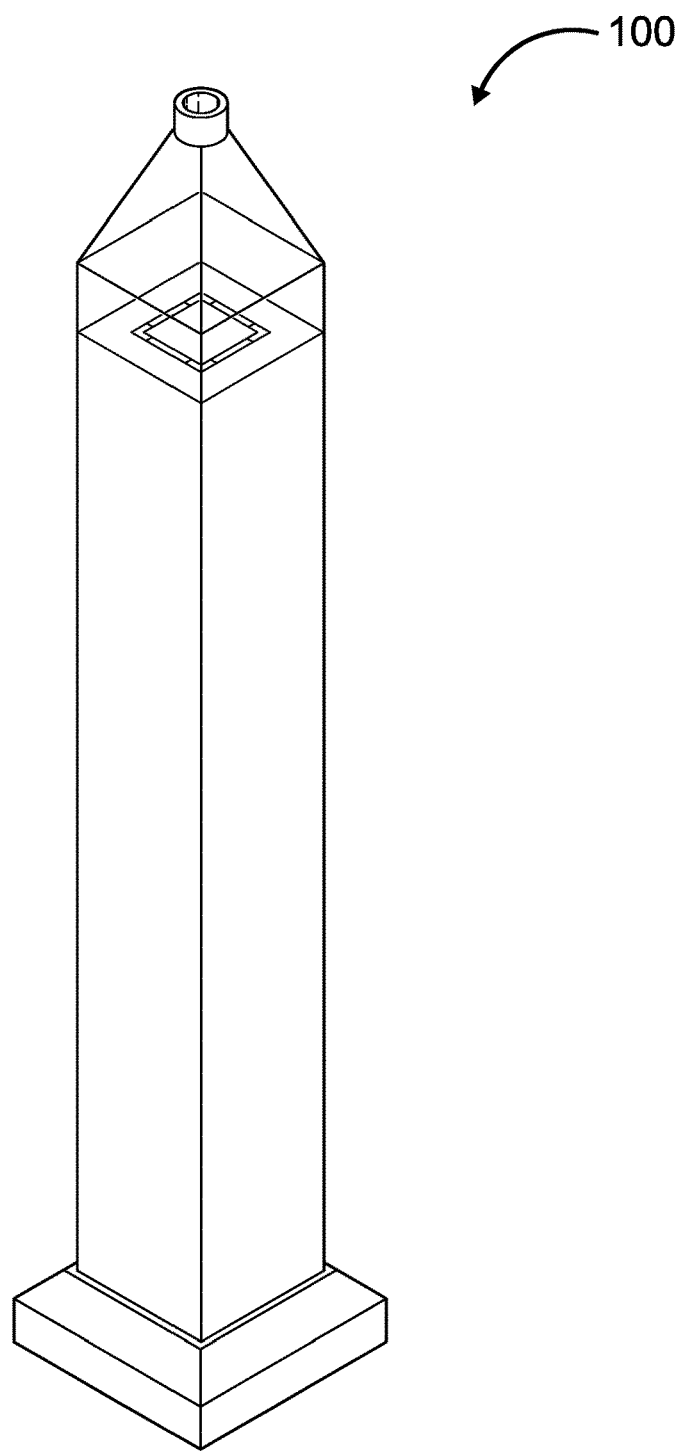
FIG. 3B is an image of the embodiment shown in FIG. 3A but also includes a cross-sectional view of the interior of the perimeter fill syringe.
Figure 4:
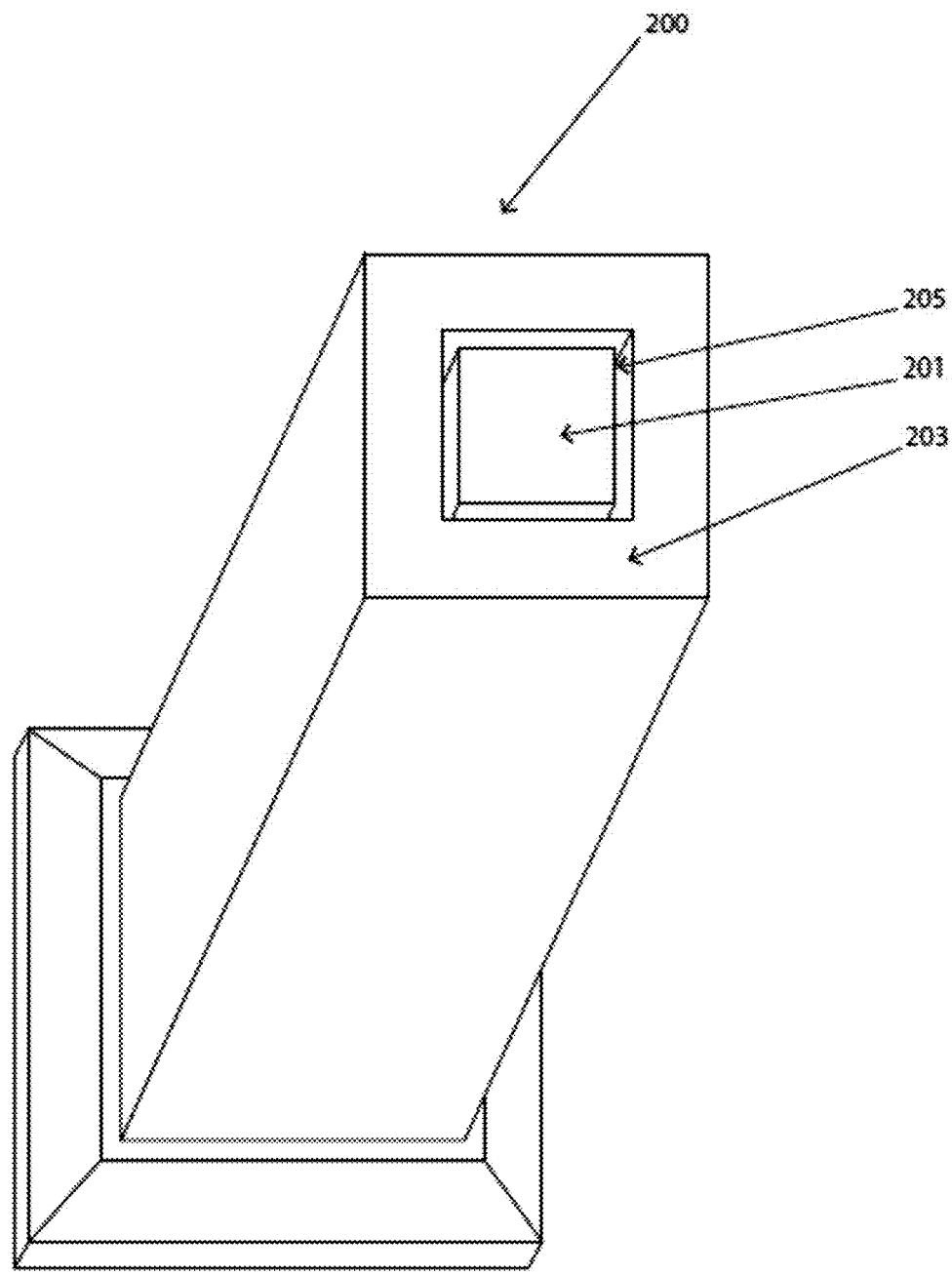
FIG. 4 is a cross-sectional view of an intermediate portion along the length of the perimeter fill syringe.
Figure 5A:
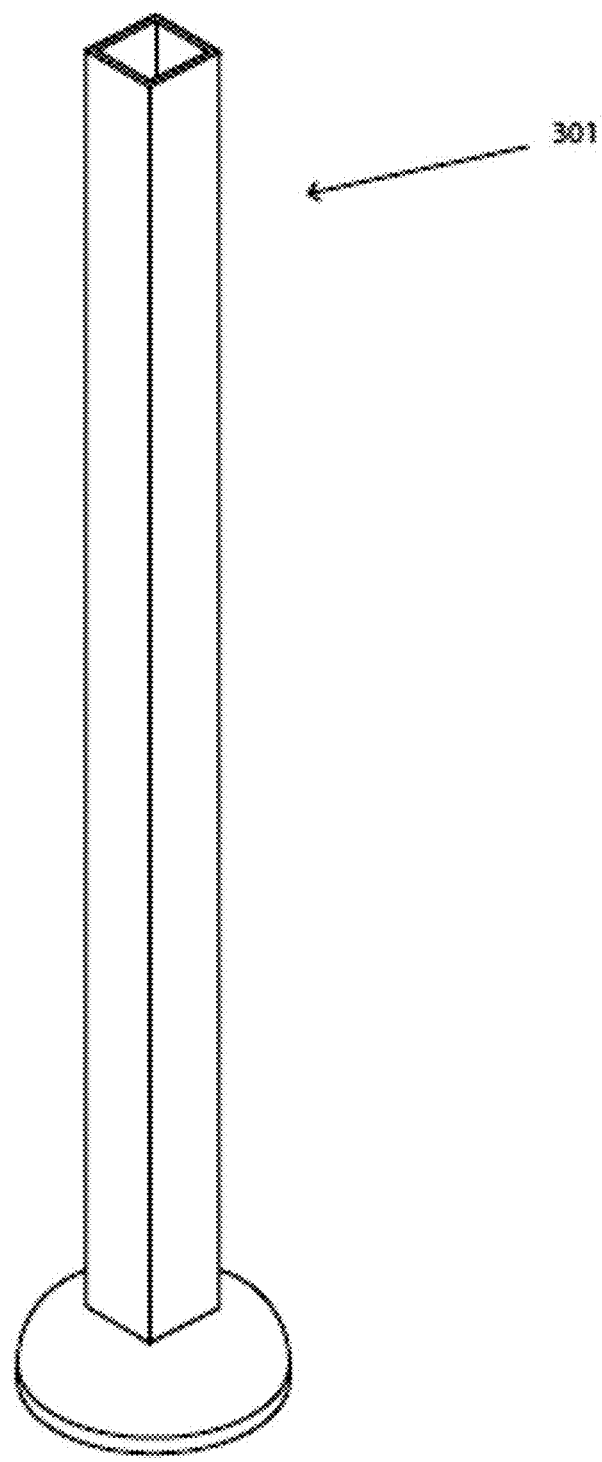
FIG. 5A shows an embodiment of the plunger that is configured to be inserted into a perimeter fill syringe that has a rectangular shape.
Figure 5B:
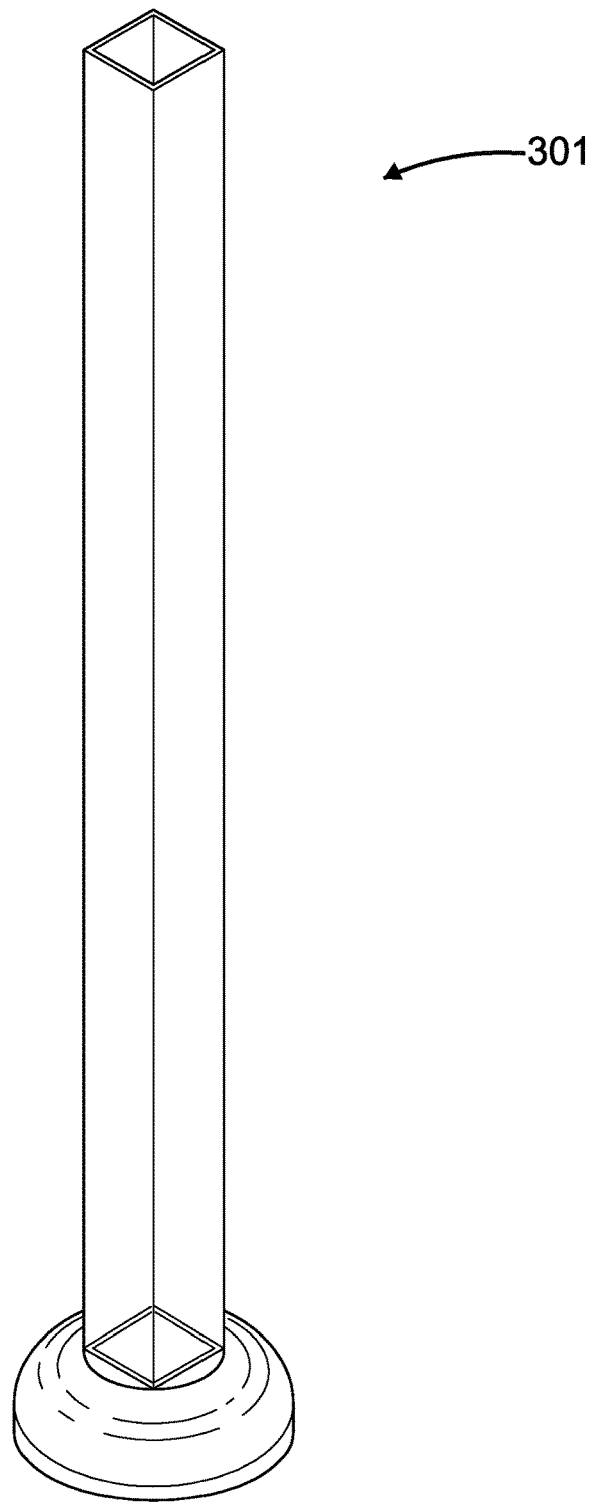
FIG. 5B is an illustration of the embodiment shown in FIG. 5A.
Figure 6:
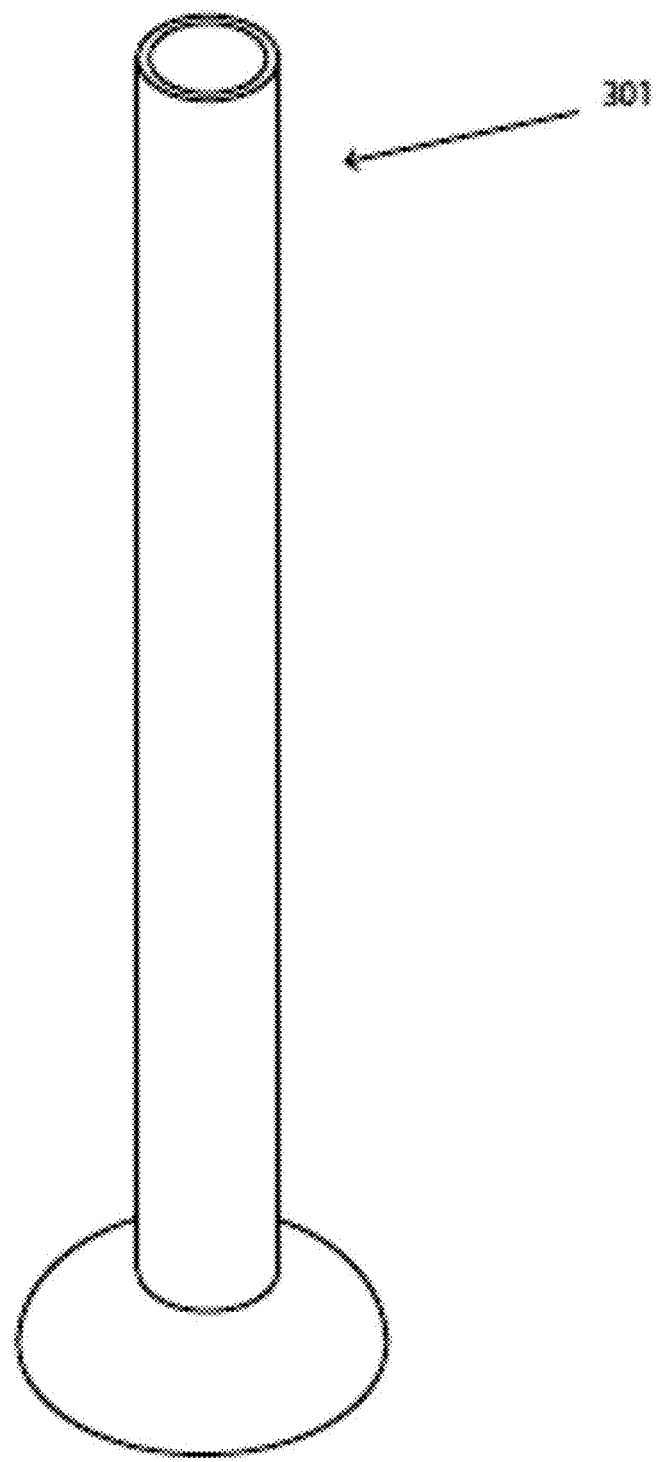
FIG. 6 is an image of an embodiment of the plunger that is configured to be inserted in to a perimeter fill syringe that has a cylindrical shape, such as that in FIG. 2A.

To address the above concerns, a novel design for a syringe, hereinafter referred to as a "perimeter fill syringe" is disclosed. Referring to FIGS. 2A and 2B, in one embodiment, the perimeter fill syringe 100 is cylindrical in shape. In another embodiment, referring to FIGS. 3A and 3B, the perimeter fill syringe 100 is of a rectangular shape. It should be appreciated that although for demonstration purposes of this disclosure a cylindrical and rectangular shape for the perimeter fill syringe 100 are described, such descriptions are not intended to be limiting, and rather, any shape can be used. Referring to FIG. 4, which is a cross-sectional view of an intermediate portion 200 along the length of the perimeter fill syringe 100, the perimeter fill syringe 100 and has a core 201. Still referring to FIG. 4, an outer shell 203 encases the core 201. In between the outer shell 203 and the core 201 is a fluid space 205 for the medication or fluid to be placed. Referring to FIGS. 5A and 5B, a plunger 301 is configured to be inserted into the fluid space 205. FIGS. 5A and 5B show an embodiment of the plunger 301 that is configured to be inserted into a perimeter fill syringe 100 that has a rectangular shape. FIG. 6 shows an embodiment of the plunger 301 that is configured to be inserted in to a perimeter fill syringe 100 that has a cylindrical shape.

Referring to FIG. 2B, an image of an embodiment of the top end 204 of the outer shell 203 of the perimeter fill syringe 100 is shown, of which the plunger 301 shown in FIG. 6 can be inserted. The fluid space 205 is no longer along the shape of a ring at the top end 204 of the outer shell 203 to allow for minimal waste of the medication or fluid traveling through the fluid space 205.

Figure 7:
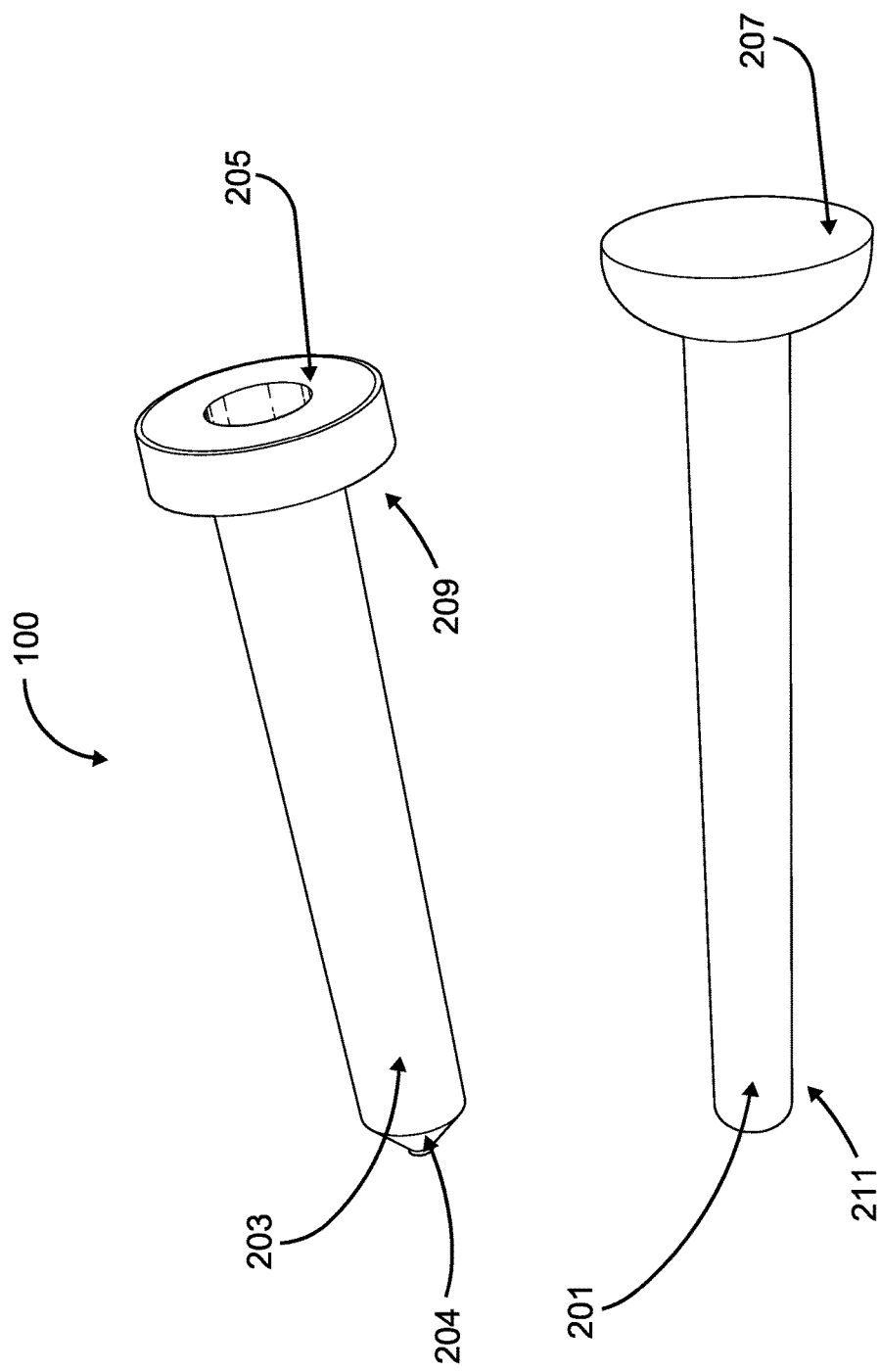
FIG. 7 shows separate images of the core and of the outer shell of an embodiment of the perimeter fill syringe.

Referring to FIG. 7, which shows separate images of the core 201 and of the outer shell 203 of an embodiment in which the perimeter fill syringe 100 is in cylindrical in shape, the top end 204 of the outer shell 203 can be configured to have a syringe needle inserted thereon. Still referring to FIG. 7, the core 201 can have a bottom end 207 that is configured to be coupled to a plunger that can facilitate the core 201 being inserted into the outer shell 203 to thereby administer the medication through the fluid space 205. A space for the plunger needs to be configured into the design of the perimeter fill syringe 100, an example of which is shown at the top of FIGS. 3A and 3B. FIG. 8 similarly shows an alternate embodiment of the perimeter fill syringe 100 shown in FIG. 7, but in FIG. 8, the shape of the perimeter fill syringe 100 is rectangular. FIG. 4 shows an alternate view of the embodiment of the perimeter fill syringe 100 of FIG. 8. Referring to FIG. 7, the fluid can be inserted into the fluid space 205 can be seen to form the shape of a ring along a bottom portion 209 of the perimeter fill syringe 100. Still referring to FIG. 7, the top end 211 of the core 201 is configured to be inserted into the bottom portion 209 to fill the fluid space 205.

Figure 9A:
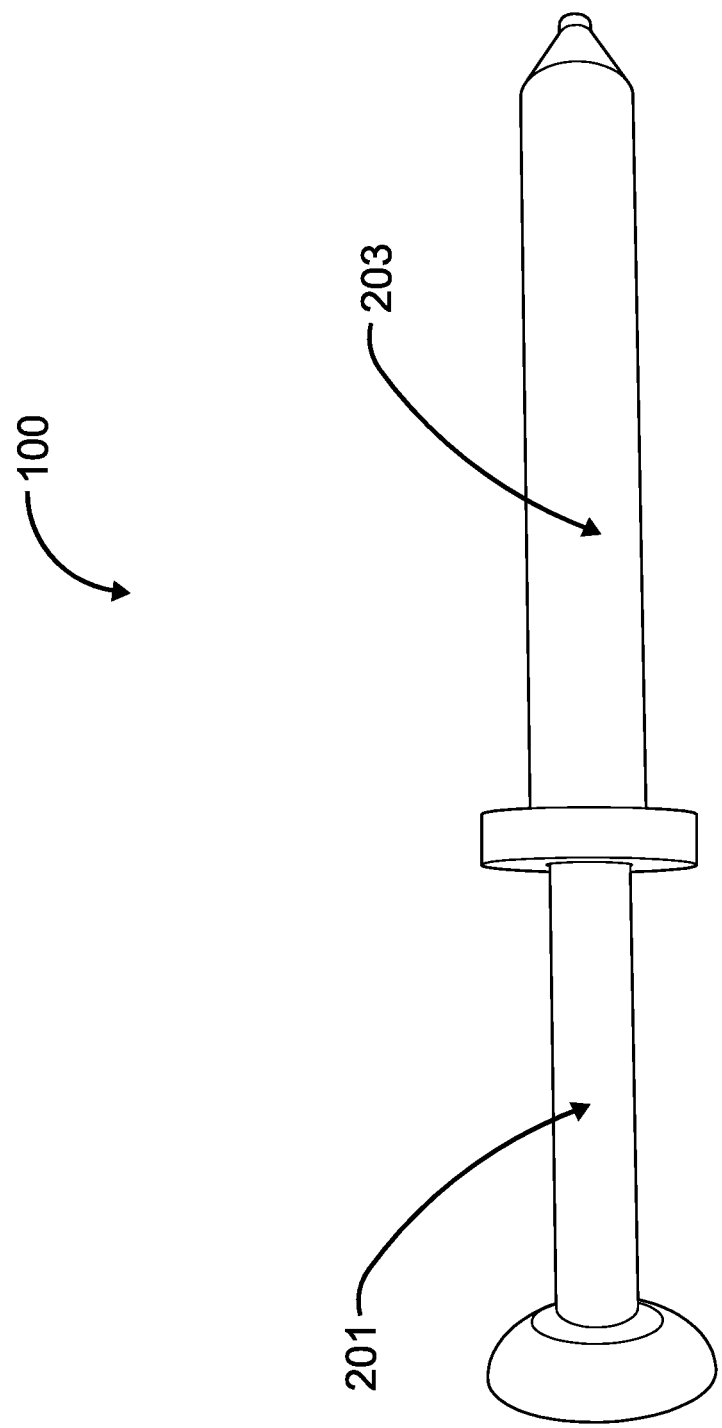
FIG. 9A shows an embodiment of the fully assembled perimeter fill syringe, wherein the core is partially slidably inserted into the outer shell.
Figure 9B:
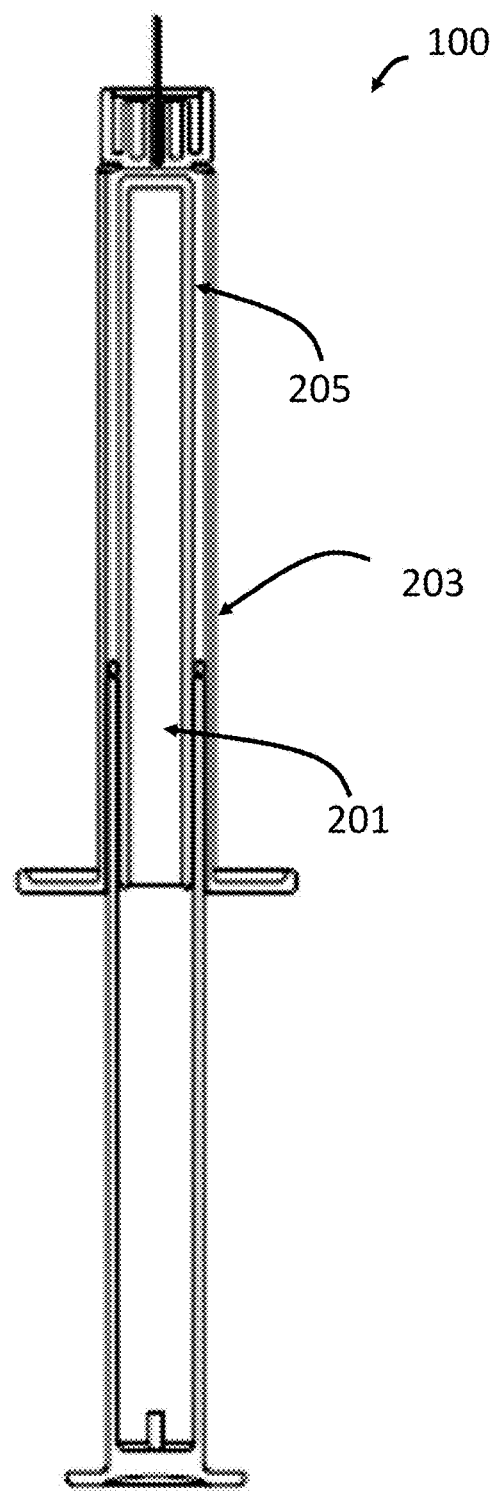
FIG. 9B shows an image of an embodiment of a fully assembled perimeter fill syringe.

FIGS. 9A and 9B show an embodiment of the fully assembled perimeter fill syringe 100, wherein the core 201 is partially slidably inserted into the outer shell 203. Referring to FIG. 9B, drawing back the core 201 allows the fluid space 205 to fill with fluid medication. Such a thin perimeter geometry enables a wider syringe design that is easier to grasp for patients and health care providers, especially those with lessening of motor function or dexterity. The wider diameter on the perimeter fill syringes 100 also enables markings to appear more clearly on a single face of the perimeter fill syringe 100, thus eliminating the need to roll or rotate the syringe in a user's hand while drawing up a dosage of medication.

As described above, the perimeter fill syringes 100 can take on a plurality of shapes and geometries. For instance, the perimeter fill syringe 100 can be of a cylindrical shape. Alternatively, a rectangular prism-like shape can be used. Yet another embodiment features a triangular prism-like shape for the perimeter fill syringe 100.

Table 1 shows an example of the calculations for a 500 unit syringe and various inner width dimensions, specifically for estimating a desired fluid space 205 for a perimeter fill syringe 100 that is rectangular in shape and the core 201 and outer shell 203 each have widths that are the same (i.e., their top and bottom ends are squares), given the dimensions of the outer shell 203 and the core 201, for a desired height of the perimeter fill syringe, and an inner width core 201 diameter. Such calculations are conducted using volume dimensions and the exact calculations can vary depending on the geometry of the perimeter fill syringe 100 (e.g., volumetric calculations for a cylinder can be used if the perimeter fill syringe 100 is cylindrical; volumetric calculations for a triangle will be used if the perimeter fill syringe 100 is triangular). The fluid space 205 needs to be calculated such that the plunger will not cripple with the force of drawing the fluid in and out of the perimeter fill syringe 100.

rectangular shape of the U500 insulin syringe acts as a physical alert and a forcing function to warn both patients and nurses alike that this syringe contains highly concentrated insulin. Using this new invention, a new standard will be set for administration of insulin. The cylindrical shape will be retained for U100 insulin while the rectangular shape will become the new standard by which all 500 unit/mL insulin will be dispensed and administered. Changing the shape of the syringe is a human factors strategy that will reduce the cognitive load on nurses and patients when they need to be focused on other matters. Now, rather than having to be extremely diligent to avoid mixing concentrations, they can consistently rely upon syringe geometry as a forcing function to prompt safe dispensing and administration techniques.

In addition to the differing syringe geometries, each syringe can have markings on the barrel or outer shell 203 that precisely correlate to the concentration of the corresponding insulin being administered. Therefore, in a U100 syringe, 0.2 mL will be 20 units every time and no dose of U500 should ever be drawn up in these syringes ever again. A U500 syringe will have 100 units marked at the corresponding 0.2 mL line on the barrel because only 500 unit/mL insulin shall ever be used in this shape of syringe. Keeping the markings distinct eliminates the need for additional math and calculations or incorrect labeling on the barrel after drawing up insulin.

TABLE 1

Sample Fluid Space and Dimension Calculations for a 500 unit syringe

| Height of intermediate space between the top and bottom of the outer shell | Inner Width (i.e., radius of the square that forms the inner perimeter of the fluid space) (i.e., the width of the core) | Outer Width (i.e., the radius square that is the outer perimeter of the fluid space (i.e., the inner cutout portion of the outer shell)) | Fluid Space |
|---|---|---|---|
| 4 | 0.1 | 0.367423 | 2.67435 |
| 4 | 0.15 | 0.384057 | 2.340573 |
| 4 | 0.2 | 0.40620192 | 2.062019 |
| 4 | 0.25 | 0.433013 | 1.830127 |
| 4 | 0.3 | 0.463681 | 1.636809 |
| 4 | 0.35 | 0.497494 | 1.474937 |
| 4 | 0.4 | 0.533854 | 1.338539 |
| 4 | 0.45 | 0.572276 | 1.222762 |
| 4 | 0.5 | 0.612372 | 1.123724 |

The exact dimensions can vary depending on a variety of factors, including the desired ease of flow of the particular medication to be administered and the age and physical abilities of individual administering the medication. For example, a patient with weak hands and poor dexterity may need a perimeter fill syringe 100 that is capable of having a sliding motion that has less resistance than what is considered normal in the field. Similarly, if the user of the perimeter fill syringe 100 is a child, the sliding motion may have to be altered accordingly to ensure ease of use for the patient. Alternate colors and shapes can also be used to help identify and alert the user as to which medication and dosage is being administered.

Such configurations can revolutionize the way in which medications are administered by patient and health care providers. Such designs address the issue of drawing up different concentrations of insulin into a single type of syringe. In the example given above where a health care provider walks away from two identical volumes of different concentrations of insulin, it was previously impossible to discern between the two. Now, with this disclosure, the Those skilled in the art will recognize that numerous modifications can be made to the specific implementations described above. The implementations should not be limited to the particular limitations described. Other implementations may be possible.

The invention claimed is:

1. A perimeter fill syringe, comprising:
    a top end, wherein the top end is configured to be coupled to a syringe needle;
    a bottom end, wherein the bottom end is configured to be coupled to a plunger, the plunger is configured to be slidably coupled to the perimeter fill syringe;
    an outer shell, wherein the outer shell is along the length between the top and the bottom end of the perimeter fill syringe;
    an immovable core, wherein the immovable core is encased within the outer shell, wherein the immovable core is solid, wherein the immovable core is monolithic;
    the plunger; and
    the syringe needle.

2. The perimeter fill syringe of claim 1, further comprising a fluid space, wherein the fluid space is between the outer shell and the immovable core.

3. The perimeter fill syringe of claim 2, wherein the plunger is configured to be inserted into the bottom end of the perimeter fill syringe.

4. The perimeter fill syringe of claim 3, wherein the fluid space is configured such that the plunger will not cripple with the force of drawing the fluid in and out of the perimeter fill syringe.

5. The perimeter fill syringe of claim 1, wherein the outer shell comprises markings configured to enable fluid dosage measurement.

6. The perimeter fill syringe of claim 4, wherein the outer shell is cylindrical in shape.

7. The perimeter fill syringe of claim 4, wherein the outer shell is rectangular in shape.

8. The perimeter fill syringe of claim 4, wherein the outer shell is octagonal in shape.

9. The perimeter fill syringe of claim 4, wherein the outer shell is triangular in shape.

10. The perimeter fill syringe of claim 4, wherein the outer shell is transparent.

11. The perimeter fill syringe of claim 4, wherein the outer shell is opaque.

12. The perimeter fill syringe of claim 4, wherein the outer shell is translucent.

13. A perimeter fill syringe, comprising:
   a top end, wherein the top end is configured to be coupled to a syringe needle;
   a bottom end, wherein the bottom end is configured to be coupled to a plunger, wherein the plunger is configured to be slidably coupled to the perimeter fill syringe;
   an outer shell, wherein the outer shell is along the length between the top and the bottom end of the perimeter fill syringe;
   an immovable core, wherein the immovable core is encased within the outer shell, wherein the immovable core is solid, wherein the immovable core is monolithic;
   the plunger;
   the syringe needle; and
   a fluid space, wherein the fluid space is between the outer shell and the core.

14. The perimeter fill syringe of claim 13, wherein the plunger is configured to be inserted into the bottom end of the perimeter fill syringe.

15. The perimeter fill syringe of claim 13, wherein the fluid space is configured such that the plunger will not cripple with the force of drawing the fluid in and out of the perimeter fill syringe.

16. The perimeter fill syringe of claim 13, wherein the outer shell is opaque.

17. A perimeter fill syringe, comprising:
   a top end, wherein the top end is configured to be coupled to a syringe needle;
   a bottom end, wherein the bottom end is configured to be coupled to a plunger, wherein the plunger is configured to be slidably coupled to the perimeter fill syringe, wherein the plunger is configured to be inserted into the bottom end of the perimeter fill syringe;
   an outer shell, wherein the outer shell is along the length between the top and the bottom end of the perimeter fill syringe;
   an immovable core, wherein the immovable core is encased within the outer shell, wherein the immovable core is solid, wherein the immovable core is monolithic;
   the plunger; and
   the syringe needle.

18. The perimeter fill syringe of claim 17, further comprising a fluid space, wherein the fluid space is between the outer shell and the immovable core.

19. The perimeter fill syringe of claim 18, wherein the fluid space is configured such that the plunger will not cripple with the force of drawing the fluid in and out of the perimeter fill syringe.

20. The perimeter fill syringe of claim 17, wherein the outer shell is transparent.

* * * * *